United States Patent
Vlahos

(10) Patent No.: US 7,530,954 B2
(45) Date of Patent: May 12, 2009

(54) METHOD AND APPARATUS FOR IDENTIFYING THE VALID SYSTOLIC BLOOD PRESSURE OF A PERSON WITH HARDENED ARTERIES

(75) Inventor: Petro Vlahos, Chatsworth, CA (US)

(73) Assignee: The Vlahos Family Trust, Chatsworth, CA (US)

( * ) Notice: Subject to any disclaimer, the term of this patent is extended or adjusted under 35 U.S.C. 154(b) by 597 days.

(21) Appl. No.: 11/223,308

(22) Filed: Sep. 8, 2005

(65) Prior Publication Data
US 2007/0055162 A1    Mar. 8, 2007

(51) Int. Cl.
*A61B 5/02*    (2006.01)
(52) U.S. Cl. .................... 600/490; 600/500; 600/496; 600/494
(58) Field of Classification Search ............... 600/481, 600/483, 485–503
See application file for complete search history.

(56) References Cited

U.S. PATENT DOCUMENTS

| 4,137,907 | A | * | 2/1979 | Jansen et al. | 600/494 |
|---|---|---|---|---|---|
| 4,140,110 | A | * | 2/1979 | Jansen et al. | 600/494 |
| 4,243,045 | A | * | 1/1981 | Maas | 600/508 |
| 4,664,126 | A | * | 5/1987 | Link | 600/494 |
| 4,905,704 | A | * | 3/1990 | Walloch | 600/495 |
| 5,183,051 | A | * | 2/1993 | Kraidin et al. | 600/500 |
| 5,704,362 | A | * | 1/1998 | Hersh et al. | 600/486 |
| 6,520,920 | B2 | * | 2/2003 | Nissila et al. | 600/503 |
| 6,616,612 | B1 | * | 9/2003 | Nissila et al. | 600/485 |
| 7,264,594 | B2 | * | 9/2007 | Shimazu et al. | 600/490 |
| 2001/0020134 | A1 | * | 9/2001 | Nissila et al. | 600/503 |

* cited by examiner

*Primary Examiner*—Charles A Marmor, II
*Assistant Examiner*—Navin Natnithithadha
(74) *Attorney, Agent, or Firm*—Blakely, Sokoloff, Taylor & Zafman

(57) ABSTRACT

A rising cuff pressure detects the diastolic blood pressure and continues to rise to generate a pulse amplitude profile. The systolic blood pressure is determined by a computation using data from the profile to discriminate against the contribution of a hardened artery, without requiring the cuff pressure to exceed the systolic blood pressure.

8 Claims, 3 Drawing Sheets

| CUFF PRES. | REM. PRES. | WORK DONE |
|---|---|---|
| 0 | 10 | 0 |
| 1 | 9 | 9 |
| 2 | 8 | 16 |
| 3 | 7 | 21 |
| 4 | 6 | 24 |
| 5 | 5 | 25 |
| 6 | 4 | 24 |
| 7 | 3 | 21 |
| 8 | 2 | 16 |
| 9 | 1 | 9 |
| 10 | 0 | 0 |
FIG. 3C
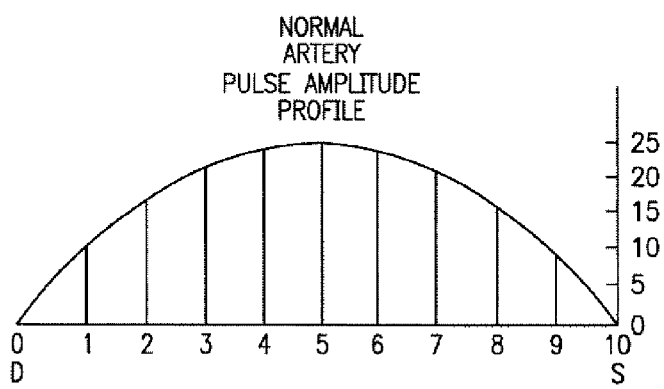
FIG. 3D
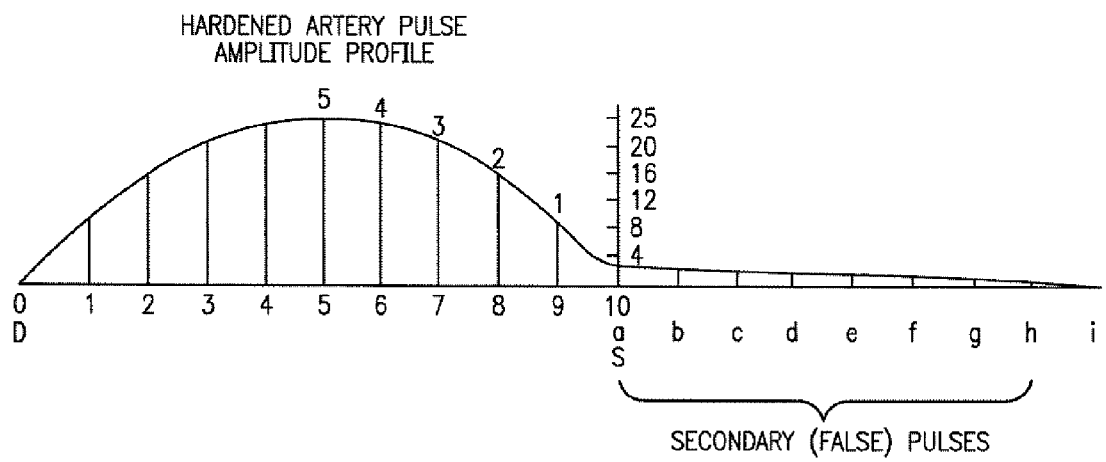
FIG. 5
   
FIG. 4A   FIG. 4B   FIG. 4C   FIG. 4D

METHOD AND APPARATUS FOR IDENTIFYING THE VALID SYSTOLIC BLOOD PRESSURE OF A PERSON WITH HARDENED ARTERIES

BACKGROUND OF THE INVENTION

It is widely known that many old people develop hardening of the arteries as they age. Arteries become stiffer, harder, and less flexible. What is not commonly known is that a hardened artery can increase the reading of the systolic blood pressure.

Blood pressure consists of two pressure levels measured in millimeters of mercury (mmHg). The diastolic blood pressure (the low number) exists between heartbeats. The systolic blood pressure, (the high number) occurs at the peak of each heartbeat.

A substantial amount of training is needed before nurses develop the skills to get consistent and comparable blood pressure readings using the arm cuff and stethoscope. Since diagnosis and medication often depend on the patient's measured blood pressure, there is a need for assured accuracy and repeatability. Many hospitals have switched to an Automatic Blood Pressure Machine, whose readings are independent of the skill or judgment of an operator.

If the method for measuring blood pressure is based on criteria that do not include the influence of a hardened artery, then blood pressure as read by the machine, or by doctors and nurses will be consistently in error for patients with hardened arteries, the very patients where accuracy is most needed.

The present method of measuring blood pressure, whether by man or machine, follows the ancient procedure of pumping up an arm cuff to a relatively high pressure to be certain it is above the systolic blood pressure of the patient. A slowly falling column of mercury (indicating pressure) is closely watched while listening to a stethoscope for a first faint audible pulse to identify the systolic blood pressure, and the last faint audible pulse to identify the diastolic blood pressure.

This procedure with cuff, stethoscope and a falling column of mercury is the standard against which blood pressure machines may be compared for accuracy. The invention described below identifies the contribution of a hardened artery that causes consistently false high systolic blood pressure readings by blood pressure measuring machines, or by a doctor using a falling column of mercury.

SUMMARY OF THE INVENTION

This invention is the result of the discovery that hardened arteries provide leakage pulses that start at and extend well above the systolic blood pressure. These pulses cause all measuring methods, using an arm cuff, to result in a systolic blood pressure reading substantially higher than the actual systolic blood pressure. This invention consists of using a rising cuff pressure to generate a pulse amplitude profile that rises to a peak amplitude then falls toward zero. The pulse amplitude profile falling to zero will never reach zero because zero will have been replaced by a first leakage pulse. The valid systolic blood pressure is obtained by extrapolating a falling pulse amplitude profile to zero in real time before the scheduled arrival of the last profile pulse. The cuff pressure at the extrapolated zero is the valid systolic blood pressure.

BRIEF DESCRIPTION OF THE DRAWINGS

FIG. 3C is a table of pulse amplitudes derived from FIG. 3B.

FIG. 3D is a pulse amplitude profile plotted from the table of FIG. 3C and is an example of the pulse amplitude profile for a person with a blood pressure of 120/80 as the cuff pressure rises from point D to S.

FIGS. 4A, 4B, 4C, and 4D show the cross section of a hardened artery being flattened by a rising cuff pressure.

FIG. 5 shows a pulse amplitude profile of a hardened artery that includes false blood pressure pulses.

DETAILED DESCRIPTION OF THE INVENTION

The term 'pulse' is used to describe ejection of blood from the heart into the arteries. This pulse can be felt by pressing the fingers onto the inside area of the wrist, where it is common to obtain ones pulse rate. The term "pulse loudness" refers to the loudness of pulse sounds one hears in a stethoscope placed over the artery during a blood pressure measurement. The term "pulse amplitude" is used instead of pulse loudness when an automatic blood pressure measuring device is used to measure blood pressure. A pressure sensor measures pressure and pulse amplitude in the arm cuff. If the pressure sensor had been connected to earphones, it would make sounds very similar to those one hears in the stethoscope.

Figure 1:
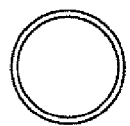
FIG. 1 shows a cross section of a normal artery when the cuff pressure is less than the diastolic blood pressure.
Figure 2:
FIG. 2 shows a cross section of a normal artery collapsed by a cuff pressure higher than that of the diastolic blood pressure.

FIG. 1 represents a soft pliable artery. Its normal shape is kept tight and round by its internal blood pressure, assume 80 mmHg. It holds this shape until a rising external cuff pressure slightly exceeds the artery's internal pressure, causing the artery to collapse to the flat shape of FIG. 2. The next pulse to arrive will cause a first faint sound, which is accepted as the diastolic blood pressure.

As the cuff pressure rises, it provides a greater force holding the artery closed. The artery stays closed until the next pulse opens the closed artery and begins delivering blood through the artery against the cuff pressure that was holding it closed.

As the cuff pressure continues to rise, pulse amplitude continues to rise to a peak and then declines to zero amplitude as cuff pressure becomes equal to the systolic blood pressure. This rise to a peak followed by a pulse amplitude decreasing to zero, is called a pulse amplitude profile. It is this profile that permits the calculation of a valid systolic blood pressure reading for the elderly.

This invention uses a rising cuff pressure, instead of a falling cuff pressure, so as never to exceed the systolic blood pressure during its measurement. It also permits the determination of blood pressure by those having arrhythmia by raising the cuff pressure in steps, where each step can be held for several pulses to find a pulse value.

The current method using a falling cuff pressure requires an initial cuff pressure well above the systolic pressure for its measurement, which can be very painful for those with high blood pressure.

Profile Generation

Figure 3A:
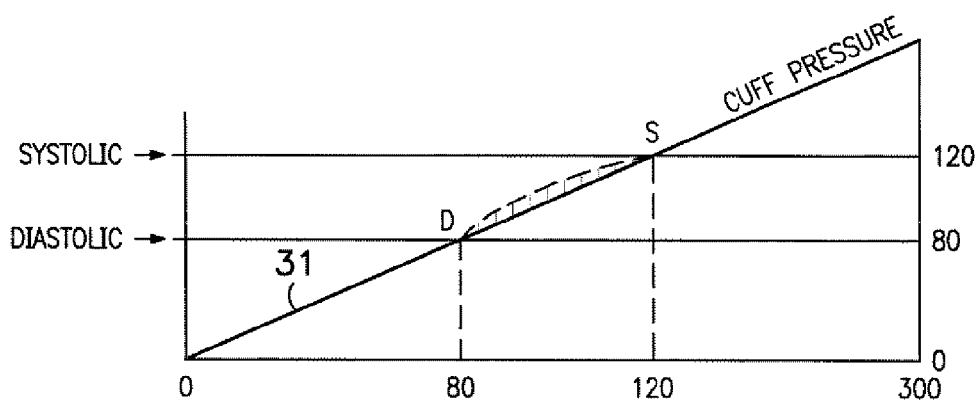
FIG. 3A is a graph showing a rising cuff pressure intersecting the diastolic blood pressure line and the systolic blood pressure line with pulses between them.

It was explained above that the first faint sound and the last faint sound, of a falling cuff pressure, defined the systolic and diastolic blood pressures. This is true for nearly everyone except old people with hardened arteries. To determine their systolic blood pressure one needs to generate a Pulse Amplitude Profile. FIG. 3A aids in the explanation of its generation.

The line 31 slanting upward is cuff pressure, starting at zero, and intersecting the Diastolic blood pressure line at point D, (assume 80 mmHg), and continues upward to intersect the Systolic blood pressure line at point S, (assume 120 mmHg). The area of interest is between points D and S as shown enlarged in FIG. 3B. The pulse amplitude profile of 3D is developed from this area.

Figure 3B:
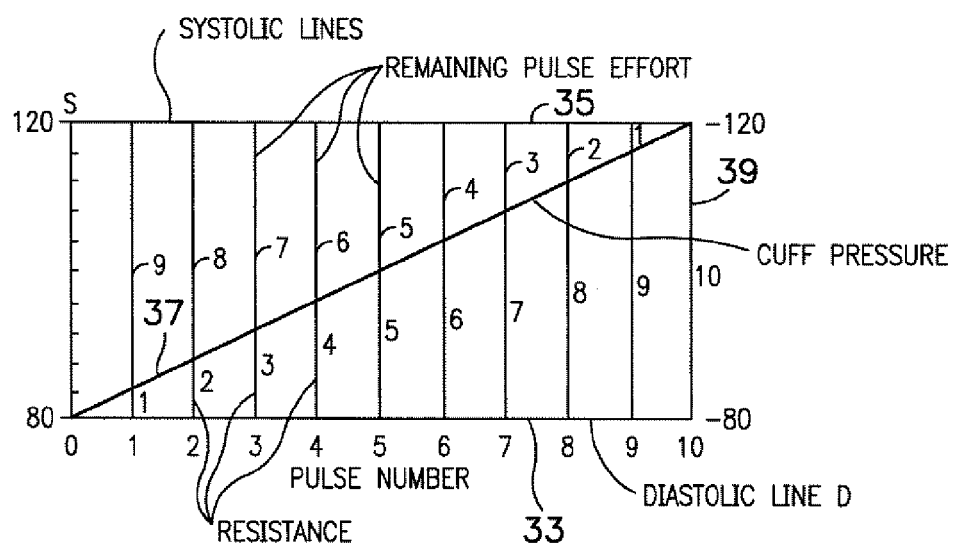
FIG. 3B illustrates the distribution of work done at each pulse as a function of cuff pressure in a pulse amplitude profile.

FIG. 3B shows a bottom horizontal line 33 at 80 mmHg, the diastolic blood pressure, and a top horizontal line 35 at 120 mmHg, the systolic blood pressure. One is 40 mmHg above the other. This 40 mmHg difference can be divided into 10 steps of 4 mmHg, which is convenient for describing the generation of the pulse amplitude profile. The sloped line 37 indicates a rising cuff pressure beginning at 80 and ending at 120. There are 11 pulses in FIG. 3B shown as vertical lines 39 beginning at position zero, and ending at position 10. Each pulse begins at the diastolic line and rises vertically to the systolic line. The sloped cuff pressure line 37 is shown to rise from point D the diastolic pressure line, up to the systolic pressure line at point S. At this point the cuff pressure is equal to the systolic blood pressure at point S, which defines the systolic blood pressure.

Work is defined as the product of force times distance. The amount of work done by each pulse determines its pulse amplitude. At position zero there is nothing to restrict a pulse of blood from silently passing through the artery under the cuff since it is not being resisted by cuff pressure.

The table of FIG. 3C begins with position zero, and cuff pressure 80 (shown as 0 in the table), and work done as zero. At position 1, in FIG. 3B, the cuff pressure is at one unit above the diastolic pressure and this is the pressure that must be reached by a pulse before the artery opens to permit blood flow. However, all the time that blood flows, it is pushing against a cuff pressure of 1 unit above the diastolic pressure. Table 3C shows position 1 to have a cuff pressure of 1 unit above the diastolic pressure, a work time of 9, and their product (work done) is 9. The table shows position 2 at two units of cuff pressure, 8 units of work time, and 16 units of work done. 'Work done' keeps increasing up to line 5, then it begins decreasing, even though cuff pressure is still rising.

Position 5 shows a cuff pressure of 5 units, and a remaining work time of 5 units above the cuff pressure. This means that the pulse had to start pushing for half its available time to reach the cuff pressure that opens the artery, and holds it there while forcing blood past this pressure. As seen in the table of 3C, position 5 performs the most work and generates the highest pulse amplitude. At position zero there was zero resistance, therefore zero work, and therefore zero sound. At position 10 the systolic pressure just equaled the cuff pressure, leaving no remaining pressure to do work, and it too is silent. When plotted, the data in table 3C becomes the profile of FIG. 3D. There are no pulse sounds for cuff pressures below point D, and there should be no sounds above point S, for persons with normal arteries. This pulse amplitude profile contains the information needed to compute the valid systolic blood pressure of a person with hardened arteries.

An existing patent, U.S. Pat. No. 6,719,703 B2, uses a pulse amplitude profile, similar to that of FIG. 3D in developing a blood pressure measuring device, which also fails to determine a valid systolic blood pressure for the reasons discussed here. A profile as shown in FIG. 3D, developed as described earlier, with the aid of FIG. 3B and table 3C is universal. Everyone has a pulse amplitude profile, but it requires a proper blood pressure measuring device to generate and record it. FIGS. 3A, 3B, 3C and 3D explain their existence.

The profile of FIG. 3D assumes the artery is suspended in a liquid. In a person, the artery is surrounded by and attached to flesh. The almost unrestricted artery just above the diastolic pressure provides higher profiles than shown in FIG. 3D, which causes the peak pulse amplitude to move closer to position 4.

The unique feature of a pulse amplitude profile is its ability to accurately identify the diastolic and systolic blood pressure. If there is any question, either end of the profile may be extrapolated to zero which accurately defines the diastolic and systolic blood pressures.

The above discussion of a pulse amplitude profile permits a comparison of the profile of the normal artery, with the profile of a hardened artery of an elderly person. It is this difference that lead to the discovery of the cause of blood pressure errors in reading the blood pressure of the elderly.

Hardened Arteries

FIG. 4A is a hardened, and less pliant artery, possibly thickened with plaque, typical of many elderly people. Cuff pressure, beginning at zero, is slowly raised to equal the patient's diastolic blood pressure. At a few millimeters above diastolic pressure, the cuff pressure causes the round artery of FIG. 4A to collapse to the flat shape with the open edge loops of FIG. 4B. Following each pulse, rising cuff pressure immediately returns the artery to a flat shape and holds it there while waiting for the next pulse. At each pulse the loops disappear to become part of the opened artery. As the cuff pressure continues to rise, the edge loops get smaller. At the systolic pressure, the loops are quite small as shown in FIG. 4C.

At a cuff pressure equal to the systolic pressure, the artery does not open to make a pulse sound, but a full strength pulse is still present and sends jets of blood through the small edge loops to generate small pulse sounds having a pssp, pssp, sound instead of thump, thump. These small pulses begin at point a, of FIG. 5, the exact position where the falling profile would have been zero. These pulses fall almost imperceptibly through points b c d e f g h, and then silence. These lettered pulses are generated by higher cuff pressures forcing the artery edge loops of FIG. 4C into the fully flat shape of FIG. 4D.

All of the lettered pulses are above the systolic blood pressure. These pulses are real in that they exist, but they are false because these secondary pulses are all above the systolic blood pressure where no pulse should exist.

Current practice accepts the first faint pulse of a falling cuff pressure as the systolic blood pressure. The first faint pulse of the profile of FIG. 5, is likely to be point h or g. This first pulse is not the systolic blood pressure. Blood pressure machines make the same error by looking for this first faint pulse. It should be noted that the transition from 5 4 3 2, 1, to a b c d e f g h, is perfectly seamless and undetectable by any known blood pressure measuring method using an arm cuff.

If FIG. 5 was to be displayed, one could see this transition point and put his finger at the profile zero. There are other methods of separating the falling profile from the secondary pulses including a limit on the radius of the profile that it may not become negative, which it must do to follow the false pulses. One could also use a limiting mask that restricts the profile from reducing its curvature beyond a straight line. It would also be possible to provide an offset raising the detection level just above the lettered pulses. The preferred method is to extrapolate the profile to zero level.

A piece of tubing of flexible rubber, plastic or other material including a hardened artery, when under sufficient external pressure will always collapse to the shape of FIG. 4B, a flattened tube with open loops at its edges. The small diameter of the open loops require considerably more force to flatten than the larger diameter of the round tube or artery.

In consideration of the physics of edge loops in collapsed tubes, and the uncertain shape of plaque lining the artery, there is no other credible explanation for the long series of pulses above the systolic pressure. The length of this string of secondary pulses is an indication of an artery's hardness, and while painful for the patient, they may be displayed for a doctor's information. It is this train of false pulses that has defeated many blood pressure measuring devices when attempting to read blood pressure of the elderly.

The profile in FIG. 5 should have ended at point S, as it did in FIG. 3D. The pulse amplitude profile falling to zero, to identify the systolic blood pressure, will never reach zero because zero will have been replaced by a first leakage pulse, pulse 'a', the first of a long train of leakage pulses.

There is ample information in the falling pulse amplitude profile to extrapolate this profile to predict, within a tolerance window, the amplitude of a next pulse before its arrival. When the predicted pulse amplitude is at zero, the cuff pressure at this extrapolated zero is the valid systolic blood pressure for older patients with hardened arteries. It is also the correct systolic blood pressure for young arteries. Cuff pressure should be deflated at the moment the extrapolated zero is known, for the comfort of the patient.

For each individual patient there is a ratio between the systolic and diastolic blood pressure. The first measurement of valid systolic and diastolic blood pressures establishes this ratio as systolic/diastolic. Measuring the diastolic pressure, therefore predicts the systolic pressure. Any significant change in the diastolic blood pressure is a reason for rechecking the systolic/diastolic ratio.

The ability to determine the systolic blood pressure while cuff pressure is at or significantly below the systolic pressure, reduces stress and pain of those suffering from high blood pressure. The reduction of cuff pressure is especially important for those patients taking Coumadin, to prevent arm bruising. Knowing the actual systolic blood pressure should reduce or eliminate the medication of a number of old people being treated for high blood pressure.

Implementation

The mechanical parts to construct a blood pressure measuring device to perform the functions described above, such as an air pump, storage tank, valves, pressure cuff, and stand with castors, are available off the shelf. The electronic parts such as a pressure sensor, display panel, switches, push buttons, memory for data and program storage, clock and data processing are available from several sources. The programs stored in the memory for control of cuff pressure, as well as a program for computing the extrapolation of said generated profile, and the subtraction of said cuff pressure from said rising cuff pressure with superimposed pulses are described with the assistance of FIG. 6.

Figure 6:
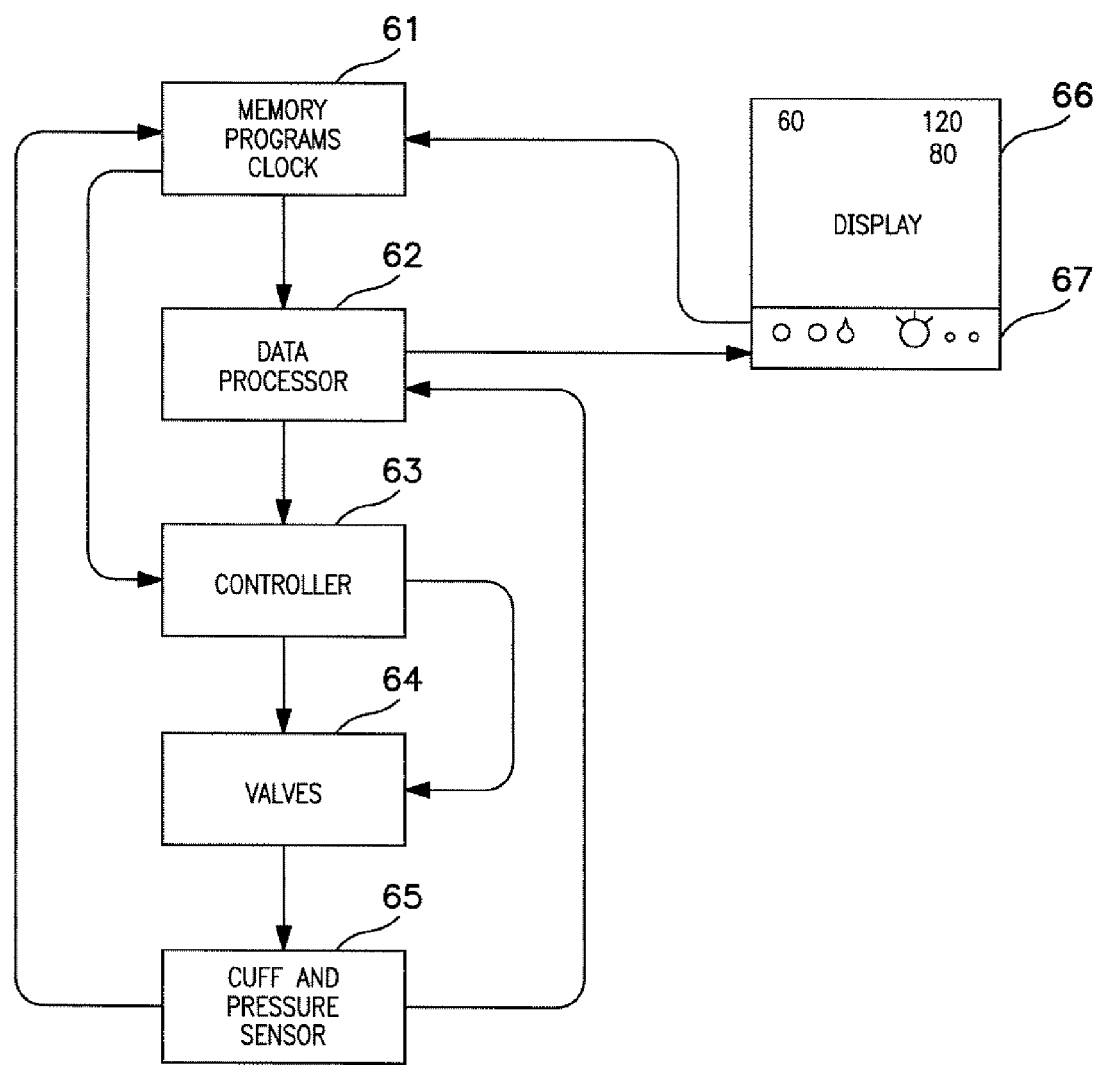
FIG. 6 is a block diagram of the functions of memory, data processing, cuff pressure feedback, and display.

Memory 61 of FIG. 6 is a memory for holding cuff inflation programs, including a program providing a uniform rise of cuff pressure, a two rate inflation program that hastens the inflation up to a level approaching diastolic pressure, followed by a uniform rise to the systolic level. A third cuff inflation program is a stepped inflation that can be held constant for several of the rapid unequal pulses of a patient with arrhythmia.

From control panel 67 a selected inflation program is routed to memory unit 61 that provides data processor 62 the instructions for controller 3 which has enough power to operate a valve 65 releasing air from a storage tank. A pressure sensor in or near the arm cuff 65, feeds the existing pressure back to processor 62 so that it may be continuously corrected. The pressure sensor in cuff 65 is also connected to memory 61 so as to record cuff pressure including all of the superimposed pulses which begin at the diastolic blood pressure.

Cuff pressure line 37 when subtracted in data processing 62, from the cuff pressure with pulses, leaves only the pulses evenly spaced sitting on a horizontal line. The amplitude of these pulses form the pulse amplitude profile. It may be displayed on monitor 66.

It is difficult to obtain a perfectly uniform rising cuff pressure, even when being continuously corrected. A clock records the time each pulse arrives and also the cuff pressure. In constructing a pulse amplitude profile, all pulses comprising said profile are re-spaced to place the pulse amplitude at the cuff pressure existing at the time of its arrival. This re-spacing causes a very smooth profile as though rising cuff pressure was truly linear. While the development of a 10 second profile may be adequate, a 15 second profile (15 pulses) provides a smoother profile.

The falling pulse amplitude can be extrapolated in processor 62 to predict a zero pulse amplitude before a false pulse arrives. As soon as the extrapolated zero pulse amplitude is known, the pressure cuff is deflated on instruction from processor 62 to controller 63.

There is no need to produce the false (secondary) pulses above the systolic blood pressure since they are not needed, and cause pain to the patient. The display of the profile including false pulses is available from the control panel, at the request of the doctor. The programming and data processing required are elementary.

I claim:

1. A method for identifying a valid systolic blood pressure of a person having hardened arteries comprising, inflating an arm cuff on a patient beginning at zero cuff pressure at a rate sufficient to detect each pulse and pulse amplitude;

detecting each said pulse and said pulse amplitude, and a cuff pressure;

transferring said pulse amplitude and said cuff pressure to a data processor as each pulse is detected;

tracking the pulse amplitude and said cuff pressure being delivered to said data processor to form a series of points representing pulse amplitude that form a curved arch typical of a section of a blood pressure profile and said series of points;

extrapolating said curved arch to predict the amplitude of a next point before a next pulse has arrived;

wherein the step of inflating the arm cuff, the step of tracking the pulse amplitude and the cuff pressure, and the step of extrapolating the curved arch is continued until the next pulse is computed by extrapolation to have zero pulse amplitude;

identifying said valid systolic blood pressure as the cuff pressure at said zero pulse amplitude; and determining said valid systolic blood pressure without the cuff pressure reaching or exceeding said valid systolic blood pressure.

2. The method of claim 1, wherein said inflating the arm cuff follows a selected programmed sequence stored in said data processor.

3. The method of claim 1, wherein said inflating the arm cuff is a programmed dual rate to quickly raise arm cuff inflation toward said diastolic cuff pressure.

4. The method of claim 1, wherein a first pulse detected using a rising cuff pressure is said diastolic blood pressure.

5. The method of claim 3, wherein said cuff inflation rate is linear with respect to time.

6. The method of claim 1, wherein said amplitude of said next point is restricted to a window consistent with said curved arch.

7. The method of claim 2, wherein said selected programmed sequence will inflate the cuff in uniform steps of cuff pressure, and wherein said uniform steps are held at a fixed cuff pressure until said next pulse arrives.

8. The method of claim 2, wherein said inflating the arm cuff occurs in uniform steps of increasing cuff pressure that may be held for the arrival of more than one pulse to obtain a stable pulse amplitude.

\* \* \* \* \*